(12) United States Patent
Schwarz

(10) Patent No.: US 11,246,646 B2
(45) Date of Patent: Feb. 15, 2022

(54) BIPOLAR SURGICAL INSTRUMENT COMPRISING A REUSABLE HANDLE AND A SINGLE-USE TOOL

(71) Applicant: Aesculap AG, Tuttlingen (DE)

(72) Inventor: Tina Schwarz, Rottweil-Gölldorf (DE)

(73) Assignee: AESCULAP AG, Tuttlingen (DE)

( * ) Notice: Subject to any disclaimer, the term of this patent is extended or adjusted under 35 U.S.C. 154(b) by 1049 days.

(21) Appl. No.: 15/524,063

(22) PCT Filed: Nov. 2, 2015

(86) PCT No.: PCT/EP2015/075411
§ 371 (c)(1),
(2) Date: May 3, 2017

(87) PCT Pub. No.: WO2016/071263
PCT Pub. Date: May 12, 2016

(65) Prior Publication Data
US 2017/0333115 A1    Nov. 23, 2017

(30) Foreign Application Priority Data
Nov. 4, 2014    (DE) .................. 10 2014 116 065.7

(51) Int. Cl.
*A61B 18/14*    (2006.01)
*A61B 17/29*    (2006.01)
(Continued)

(52) U.S. Cl.
CPC .......... *A61B 18/1445* (2013.01); *A61B 17/28* (2013.01); *A61B 17/2909* (2013.01);
(Continued)

(58) Field of Classification Search
CPC . A61B 17/28; A61B 17/2909; A61B 18/1445; A61B 2017/0046;
(Continued)

(56) References Cited

U.S. PATENT DOCUMENTS

| 3,641,479 A |   | 2/1972 | O'Brien et al. |
| 4,347,842 A | * | 9/1982 | Beale .................... A61B 18/14 604/20 |

(Continued)

FOREIGN PATENT DOCUMENTS

| DE | 202009014091 U1 | 12/2009 |
| EP | 0697199 A1 | 2/1996 |

(Continued)

OTHER PUBLICATIONS

Notification of Reasons for Rejection for Japanese Application No. 2017-523200, dated Oct. 2, 2018, with translation, 11 pages.

(Continued)

*Primary Examiner* — Tigist S Demie

(57) ABSTRACT

A surgical instrument includes a hand piece having a fixed branch and a displaceable branch for actuating a first tool and/or second tool, a guide device in which a force transmission device is arranged to be displaceable longitudinally and/or rotationally, the force transmission device coupled, on the proximal side, to the fixed branch and/or displaceable branch and coupled, on the distal side, to the first tool and/or second tool, and a connection device on which the guide device can be coupled to the hand piece in an insertable and detachable manner by a coupling simultaneously providing a holding force for holding the guide device in the connection device, a bipolar electrical contact on the distal side of the hand piece for parts of the instrument requiring energy, and degrees of freedom for longitudinal and/or rotational movement of the guide device and/or force transmission device.

10 Claims, 3 Drawing Sheets

(51) Int. Cl.
  *A61B 18/00* (2006.01)
  *A61B 18/12* (2006.01)
  *A61B 17/28* (2006.01)
  *A61B 17/00* (2006.01)

(52) U.S. Cl.
  CPC ............. *A61B 2017/0046* (2013.01); *A61B 2017/00477* (2013.01); *A61B 2017/2924* (2013.01); *A61B 2017/2925* (2013.01); *A61B 2018/00172* (2013.01); *A61B 2018/00178* (2013.01); *A61B 2018/00922* (2013.01); *A61B 2018/126* (2013.01); *A61B 2018/1495* (2013.01)

(58) Field of Classification Search
  CPC .. A61B 2017/00477; A61B 2017/2924; A61B 2017/2925; A61B 2018/00172; A61B 2018/00178; A61B 2018/00922; A61B 2018/126; A61B 2018/1495
  See application file for complete search history.

(56) References Cited

U.S. PATENT DOCUMENTS

| | | | | |
|---|---|---|---|---|
| 5,814,043 | A * | 9/1998 | Shapeton | A61B 18/14 606/41 |
| 6,074,386 | A | 6/2000 | Goble et al. | |
| 6,238,394 | B1 | 5/2001 | Garito et al. | |
| 2012/0116261 | A1 | 5/2012 | Mumaw et al. | |
| 2012/0116388 | A1 * | 5/2012 | Houser | A61B 18/1206 606/41 |
| 2012/0330307 | A1 * | 12/2012 | Ladtkow | A61B 18/1482 606/42 |
| 2014/0064847 | A1 | 12/2014 | Hirschfeld | |

FOREIGN PATENT DOCUMENTS

| | | |
|---|---|---|
| EP | 2642418 A2 | 9/2013 |
| JP | H1024051 A | 1/1998 |
| JP | 2000502578 A | 3/2000 |
| JP | 2005538818 A | 12/2005 |
| WO | 9724073 A1 | 7/1997 |
| WO | 2004520221 A1 | 6/2004 |
| WO | 2013087132 A1 | 6/2013 |

OTHER PUBLICATIONS

International Search Report and Written Opinion for International Application No. PCT/EP2015/075411, dated Feb. 5, 2016—6 Pages.
German Search Report for German Application No. 102014116065.7, dated Jul. 16, 2015—19 Pages with English Translation.
European Office Action for European Application No. 15 790 100.0, dated Apr. 26, 2017—7 Pages with English Translation.

* cited by examiner

BIPOLAR SURGICAL INSTRUMENT COMPRISING A REUSABLE HANDLE AND A SINGLE-USE TOOL

RELATED APPLICATIONS

This application is the United States national phase entry of International Application No. PCT/EP2015/075411, filed Nov. 2, 2015, which is related to and claims the benefit of priority of German Application No. DE 10 2014 116 065.7, filed Nov. 4, 2014. The contents of International Application No. PCT/EP2015/075411 and German Application No. DE 10 2014 116 065.7 are incorporated by reference herein in their entireties.

FIELD

The invention relates to a bipolar surgical instrument comprising a multi-use handle and a single-use tool as well as a connection device therebetween and especially relates to a bipolar surgical instrument comprising a connection device by means of which a surgical shank-type tool provided for single use (including an inherent shank section) can be connected in an insertable manner to a re-usable hand piece/handle. Moreover, the invention relates to a reusable handle as well as a shank-type tool of such surgical instrument.

BACKGROUND

In the field of bipolar surgical instruments especially of the minimally invasive design, from prior art for example instruments comprising bipolar tubular shank forceps/pincers are known as tubular shank tools which are operable and/or actuatable via a handle including operating elements at the proximal end of a tubular shank. Accordingly, at the distal end of the tubular shank a multi-part arrangement, for instance of the scissors, pincers or forceps type, of elements/branches linked to the tubular shank to be movable relative to each other. Inside the tubular shank a gearing extends in the form of a pull/push rod which couples the elements/branches movably linked to the tubular shank to corresponding operating elements (levers, keys, scissors holes etc.) on the handle. Manipulation of the operating elements on the handle then results in an appropriately converted movement of the movably linked elements/branches at the place of use, for example a cutting, gripping and/or rotating movement at or in the tissue of a patient.

The elements/branches furthermore are equipped with electrodes which are coupled via electric conductors inside the tool shank to control electrics inside the handle so that optionally electric current (HF current) can be applied. In those known arrangements of bipolar tubular shank instruments merely fixed connections and/or contacts between the handle and the tubular shank tool by welding and/or soldering of the respective (current-carrying) components, for example, have been used so far.

From HF surgery furthermore spring elements for monopolar instrument insertion systems are known by means of which a shank of a tubular shank tool is connectable to a handle. Inserting connections for monopolar electrodes are available according to different electrode diameters and shapes. There the monopolar electrodes can be inserted, without any further movable parts, into a spring cage-type holding arrangement within the inserting connection and can also be removed from said spring cage-type arrangement.

From the document U.S. Pat. No. 6,238,394 B1, an electrosurgical instrument is known comprising a universal handle which is designed for attaching and removing different tubular shank tools for carrying out different electrosurgical processes. For attaching and removing, the handle has a multi-part design comprising upper concave sections configured for receiving and holding the tubular shank tools. The tools are provided with similar external housing shapes so that they all fit into the concave sections. The handle parts are held together by snap-type restraining mechanisms and can be detached from each other in the same manner. The handle may receive a plurality of core tools which may comprise parts of a family of tools for both monopolar and bipolar electrosurgical processes.

Furthermore, from the document EP 0 697 199 B1 a surgical bipolar instrument is known comprising a tubular/shank-type housing into which an electrode head provided with two electrodes can be detachably inserted forming an electric connection between the electrodes and two conductors arranged in the housing. For this purpose, one conductor is formed by a conducting tubular shank electrically insulated on the outside and another conductor is formed by a rod supported in the tubular shank and being electrically insulated against the latter. One electrode includes, when the electrode head is completely inserted, inserting elements which are adjacent to the inside of the tubular shank so as to be electrically conducting, which are resiliently movable in the radial direction and which engage with a projection in a recess of the inner wall of the tubular shank or of the rod and fix the electrode in this way against axial displacement within the tubular housing. The tubular shank and the rod are movable relative to each other between a locking position and a release position in the longitudinal instrument direction, wherein the tubular shank and the rod in the locking position enclose the inserting elements between themselves in a radially non-displaceable manner with the projection engaging in the recess, whereas in the release position they enable the projection to radially exit the recess. The rod contacts the other electrode in the locking position in an electrically conducting manner.

While an electric contact of an exchangeable monopolar and/or bipolar electrode is available already, for bipolar surgical instruments, especially operable bipolar tubular shank instruments which require current and/or are designed for rotational movement, there is still demand for an insert system for connecting and/or disconnecting a tubular shank tool provided for single use to and/or from a reusable handle which insert system permits electrical contacting, fixation (mechanical coupling) of the tool to the handle as well as, at the same time, rotatability, pivotability and/or movability of parts of the tool.

SUMMARY

Therefore it is the object of the invention to provide a surgical bipolar instrument, a handle, a shank-type tool as well as a connection device for such bipolar surgical tubular shank instrument, whereby a shank-type tool provided for single use including a shank section can be detachably connected to a reusable hand piece, and which at the same time provides a fixation/mechanical coupling of the shank section, an electrical contact of elements/electrodes requiring energy in a bipolar manner and at least one rotatory degree of freedom for the shank section inside the connection device.

The general idea underlying the invention is to provide an insert system using second spring elements/spring cages/ spring collars/spring sleeves or else spring lamellas for fixing/mechanically coupling a tubular shank tool within a handle and for supplying electric current to electrodes at the tubular shank tool as well as preferably with degrees of freedom at least for rotating the tubular shank tool inside the instrument handle about the longitudinal shank axis and, optionally, for moving tool branches (on which the electrodes are arranged), which insert system is connected prior to a surgical operation and can be disconnected again after surgery. At least one spring element/cage/collar/sleeve/lamella (in the following only referred to as spring cage to simplify matters) enables, or preferably the two spring cages allow for fixation (in the longitudinal shank direction)/mechanical coupling of a tool shank within a hand piece, tight mechanical contact of immobile parts and sliding contact at least on movable parts of the shank so as to conduct electric current.

The bipolar tubular shank tool, for example bipolar tubular shank forceps or alligator forceps, for single application or for single use by the insert system, and thus a connection device or a coupling device, thus is detachably connectable to a reusable hand piece or handle so that the shank-type tool can be disposed of after use and the hand piece can be recycled and then be reused. The insert system is designed so that each time a new shank-type tool can be secured within the hand piece, i.e. is fixed/mechanically coupled and held there, so that an electrical contact of parts of the shank section requiring energy is realized by means of at least one spring element inside the insert system and, at the same time, a sliding contact enables rotatability of elements of the instrument rotatable about the longitudinal axis of the shank section while the current supply to said elements is maintained.

In other words, according to the invention inter alia a manual handle of a bipolar electrosurgical instrument preferably of the minimally invasive design is suggested comprising a current application device for optionally applying electric current (direct current or HF current) to a surgical tool by means of a power switch preferably arranged on the handle and a chuck into and from which the surgical tool can be mechanically inserted and detached at the tool shank thereof and accordingly can be electrically coupled in and out at the current application device. The chuck includes two receiving/bearing elements which are axially spaced apart in the inserting direction of the tool shank and are radially elastically yielding as well as are electrically insulated against each other for radially and/or axially guiding and/or securing the tool shank, which elements are electrically connected to the current application device so as to transmit electric current to the inserted tool.

In this way, the tool shank can be easily inserted in the chuck and can be resiliently secured against inadvertent falling out. At the same time, the elastically yielding (radially extendable) receiving/support elements provide the electric connection for the tool so that tool exchange can be safely and easily implemented.

Of preference, a handle of a bipolar surgical instrument, preferably of the minimally invasive design, is suggested comprising a current application device for optionally applying electric current to a surgical tool by means of a power switch preferably arranged on the handle and a chuck into which and from which the surgical tool can be mechanically inserted and detached at the tool shank thereof and can be electrically coupled in and out at the current application device, wherein the chuck includes two receiving/bearing elements axially spaced in the inserting direction of the tool shank, radially elastically yielding as well as being electrically insulated against each other for radially and, simultaneously, axially guiding and/or securing the tool shank, which elements are arranged to generate a clamping force producing friction fit and which are further simultaneously connected to the current application device (118, 156) in an electrical and bipolar manner and are arranged to transmit electric current to the inserted tool.

It is of advantage when each of the receiving/bearing elements forms a radially elastically extendable shank boot preferably in the form of a slip ring, a ball bearing having radially elastically movable balls or a spring cage. Preferably, the two receiving/bearing elements may be adapted to exert differently high radial forces on the inserted tool shank. It is possible in this way to grip e.g. a tool shank consisting of two nested shank rods more strongly (tightly) at its one rod and in a weaker manner (loosely) at its other rod so as to enable e.g. an axial displacement of the rod gripped in a weaker manner relative to the rod gripped more strongly at the handle.

It is advantageous when at least one of the receiving bearing elements includes a radially inwardly directed projection or a radially inwardly directed bulge. Preferably, the projection/bulge may be provided for being adapted to get into snap engagement in a radial notch/undercut for axially securing the tool shank within the chuck of the handle. In this way, the axial securing is achieved not exclusively by friction fit but by resiliently effectuated form fit.

Moreover, according to the invention a tool of a bipolar surgical instrument preferably of the minimally invasive design is suggested which is adapted to be inserted in the handle of the surgical instrument according to the foregoing definition. The tool has a tool head studded with or including electrodes at the distal end of the tool shank the proximal shank end of which is insertable into the chuck of the handle. In accordance with the invention, the tool shank includes, inter alia, two axially spaced shank sections electrically insulated against each other which are adapted to get into mechanical guiding and/or securing engagement and simultaneously into electrical contact with the two receiving/bearing elements in the chuck of the handle so as to connect the electrodes at the tool head to the current application device. Preferably, the tool is designed as a single-use article.

Further preferred, a tool of a bipolar surgical instrument preferably of the minimally invasive design is thus suggested which is adapted to be inserted into a handle of the surgical instrument preferably in accordance with any one of the afore-described embodiments, comprising a tool head studded with or including electrodes at the distal end of a tool shank whose proximal shank end is insertable into the chuck of the handle, wherein the tool shank includes two axially spaced shank sections electrically insulated against each other which are adapted to generate with the two receiving/bearing elements preferably according to any one of the afore-described embodiments in the chuck of the handle a clamping force acting on the tool shank, to guide and/or secure the tool shank radially and simultaneously axially based on friction fit produced by the clamping force and, furthermore, contact the tool shank simultaneously in an electrical and bipolar manner so as to connect the electrodes at the tool head to the current application device.

Finally, in accordance with the invention, an electrosurgical instrument of the bipolar design is suggested, comprising a handle and a tool according to the afore-mentioned definitions. In this context, it would be advantageous when the handle is provided as a reusable product and the tool is provided as a single-use product.

In other words, the bipolar tubular shank instrument is mechanically held/supported within the handle by means of two (resilient) contact (lamella) devices and at the same time is supplied with current. A contact lamella devices of preferably low force is located on a pull/push rod. The other contact lamella means of preferably high force is located on the outer tube of the tubular shank in which the push/pull rod is supported. The two parts (outer tube and push/pull rod) are electrically insulated against each other. The force of the other contact lamella device is sufficiently large so as to fix the entire shank or allow the same to merely rotate within the handle/hand piece during use. It is moreover sufficiently small so as to (manually) detach the shank from the hand piece again, if intended. The push/pull rod is supplied with current by means of a sliding contact of the one contact lamella device in which it is axially displaceable.

In a modification, the current supply is not realized by means of the rods/shanks themselves but by means of electric conductors, such as strands, and bushes for contact such that the current is not conducted by the push/pull rod and the outer tube but by the electric conductors within the tube connected to the bushes. In this case, all of the bushes are preferably arranged on the outer tube which is inserted in the handle in a fixed/merely rotating manner and therefore cannot be axially displaced. In this way, the sliding contact (arranged at the push/pull rod before) may be omitted in this configuration.

Advantages are resulting especially from the fact that the shank and the handle can be easily disconnected from each other and that plural functions (holding, supporting, electrically contacting) can be guided and, resp., realized by means of a bearing element. In accordance with the invention, thus a bipolar surgical instrument is suggested comprising a handle preferably having a fixed grip piece and a movable actuating lever for actuating a first branch and/or a second branch at the distal end of the bipolar surgical tool relative to the handle/hand piece, a shaft-type guide device (chuck) in which at the inside a bearing means for receiving the tool shank in an axially displaceable and/or rotatable manner is arranged, a force transmission device which is coupled, on the proximal side, to the fixed grip piece and/or the movable actuating lever of the handle and, on the distal side, to the first branch and/or second branch; wherein the guide device (or else connection device) is adapted for the tool shank including the force transmission device accommodated therein to be insertable into and detachable from the bearing means, wherein said insertable and detachable coupling, when in the coupled state, provides a holding force for holding the tool shank (and possibly the force transmission device) in the connection device, a bipolar electrical contact on the distal side of the tool shank for parts of the surgical instrument requiring energy, and degrees of freedom of a longitudinal movement and/or a rotational movement of the (tubular) tool shank and/or of the force transmission device. Advantageously, thus an insert system for connecting and disconnecting an instrument tool supplied with current and provided for single use and a reusable handle is realized by the contact lamellas, wherein the connection at the same time allows for rotational movement of at least parts of the tool, the current supply to the tool by means of

- at least one (quasi) fixed contact and
- an (axially acting) sliding contact or, alternatively, another (quasi) fixed contact, and
- fixation of the tool within the handle.

Of preference, the tubular tool shank is electrically insulated by an insulating element against the force transmission device supported therein; the connection device includes a first contact lamella device and a second contact lamella device each having a plurality of individual resiliently held contact lamellas; the first contact lamella device is arranged at a first position in the connection device concentrically to the longitudinal axis of the tubular tool shank and at said position contacts the outer periphery of the tubular tool shank; and the second contact lamella device is arranged at a second position in the connection device concentrically to the longitudinal axis of the force transmission device and at said position contacts the outer periphery of the force transmission device. Advantageously, in this way an insert connection is realized which establishes a bipolar electric supply of the instrument by means of merely two positions in the connection device, with further functionality being simultaneously provided at said positions. It may be of advantage, for example, when the tubular tool shank is formed to be electrically conductive at least in part. In this way, by means of the tool shank electric current can be transmitted to at least one tool element (electrode at the tool head/branch) of the surgical instrument in an especially simple manner. It may especially be provided that the tool shank is configured as a first power supply line and the force transmission device supported therein is configured as a second power supply line for supplying the at least two tool branches of the surgical instrument with current. The tool shank and the force transmission device are preferably electrically insulated against each other.

Further preferred, the first contact lamella device in a non-coupled condition has an inner diameter which is smaller than the outer diameter of the tubular tool shank, and in the coupled condition the plurality of the resiliently held contact lamellas generate a holding/clamping force acting on the outer periphery of the tubular tool shank which force is dimensioned so that, on the one hand, the tubular tool shank is safely held within the connection device (chuck) and is supplied with current for the duration of an application of the surgical instrument and, on the other hand, the tubular tool shank remains detachable from the coupled condition after application. Hence, advantageously only one contact lamella device designed to be appropriately strong is sufficient for holding the tubular tool shank tightly in the connection device so that the other contact lamella device can be dimensioned in an appropriately weaker and thus more cost-efficient manner and/or optimized as to function.

Advantageously, at the outer periphery of the tubular tool shank a recess/a formation forming an axially acting undercut is provided in which the plurality of the resiliently held contact lamellas can be locked in the coupled condition. A locking engagement advantageously provides the user with a tactile feedback about the operatively produced connecting or coupling condition (in the axial direction). Hence, prior to use the tool can be prevented from being mechanically connected to the handle in an inadvertently incomplete manner or from being supplied with current not in the intended manner. In this way, the risk of application errors in the patient is reduced.

Further preferred, the second contact lamella device in a non-coupled condition has an inner diameter which is smaller than the outer diameter of the force transmission device, and in the coupled condition the plurality of resiliently held contact lamellas generate a clamping force to acting on the outer periphery of the force transmission device which is dimensioned so that, on the one hand, the plurality of the resiliently held contact lamellas forms a sliding contact with the force transmission device adapted to be supplied with current and, on the other hand, the force transmission device remains rotationally/axially displaceable while being in sliding contact. The design of the second contact lamella device as a mere sliding contact advantageously facilitates the constructional design of the connection device.

As an alternative, it may be preferred that, on the outside of the tubular tool shank, at a first position a first contact bushing device is arranged and at a second position a second contact bushing device is arranged, wherein the first contact bushing device and the second contact bushing device are electrically insulated against the tubular tool shank by an insulating element extending over at least a predetermined length on the outer periphery of the tubular tool shank; the first contact bushing device is electrically connected to either of the branches by means of a first conductor connection and the second contact bushing device is connected to the other of the branches by means of a second conductor connection; the connection device includes a first contact lamella device and a second contact lamella device each having a plurality of individual resiliently held contact lamellas; the first contact lamella device is arranged, at the first position in the connection device, concentrically to the longitudinal axis of the tubular tool shank and at said position contacts the outer periphery of the first contact bushing device; and the second contact lamella device is arranged, at the second position in the connection device, concentrically to the longitudinal axis of the tubular tool shank and at said position contacts the outer periphery of the second contact bushing device. Two current guides for the at least two electrodes/branches and a mutual insulation are preferably replaced by one single element, i.e. the tubular tool shank. Therefore, the force transmission device may be designed to be more solid so that higher stability of the surgical instrument during use and thus less elastic deformation and better tactility will be achieved.

Further preferred, in a non-coupled condition, the first contact lamella device has an inner diameter which is smaller than the outer diameter of the first contact bushing device, and the second contact lamella device has an inner diameter which is smaller than the outer diameter of the second contact bushing device; and, in the coupled condition, each of the plurality of the resiliently held contact lamellas of the first and second contact lamella devices generates a holding force acting on the outer periphery of the first and second contact bushing devices, which holding force is dimensioned so that, on the one hand, the tubular tool shank is axially held and supplied with current safely in the connection device for the duration of an application of the surgical instrument and, on the other hand, the tubular tool shank remains optionally rotatable as well as detachable from the coupled condition after application. The splitting of the holding force to two contact lamella devices is advantageously to the effect that, when one contact lamella device is weakened, there is still provided a holding force by the second contact lamella device. Hence, on the one hand, the individual contact lamella devices are loaded more uniformly and/or less strongly and it is ensured that, in the event of break of either of the contact lamella devices during an application, the instrument is continued being axially held by the other contact lamella device and thus cannot fall out in an uncontrolled manner during application on the patient.

Advantageously, the first contact lamella device and the second contact lamella device are equally dimensioned and each of them generates the same holding force (clamping force onto the tool shank). In this way, in the case of repair or maintenance work, advantageously only one part number may be provided and the constructional design of the connection device is simplified.

As an alternative, the first contact lamella device and the second contact lamella device may be differently dimensioned and may generate different holding forces. This option may permit easier adaptation of the connection device to different tools and may offer compatibility and access to tools of third-party manufacturers for example in the form of connection devices exchangeable in the form of modules.

Advantageously, at the outer periphery of at least one of the contact bushing devices at least one formation forming a recess is provided in which at least part of the plurality of the resiliently held contact lamellas can be locked in the coupled condition. Locking engagement advantageously provides the user with a tactile feedback about the operatively established connecting and coupling condition. Thus, it can be prevented prior to an application that the tool inadvertently is not completely connected or is not supplied with current as intended. The risk of errors of application on the patient is reduced.

Preferably, the connection device further includes at least one insulating element having a first recess at the first position for receiving the first contact lamella device and having a second recess at the second position for receiving the second contact lamella device; and conductor connections for electrically connecting each of the first contact lamella device and the second contact lamella device to terminals in the hand piece are guided through the at least one insulating element. In order to be able to transmit current specifically from the surgical instrument to body parts to be subjected to surgery, at least one of the branches may be configured to be electrically conducting at least in portions. A live line required in the case of bipolar application of one branch of the surgical tool thus can be guided through the connection device in an advantageous and transparent manner without impairing the live line in the other components.

BRIEF DESCRIPTION OF THE DRAWING FIGURES

Hereinafter the invention shall be described in detail with further advantages and effects by way of preferred embodiments with reference to the drawings, wherein.

DETAILED DESCRIPTION

Figure 1:
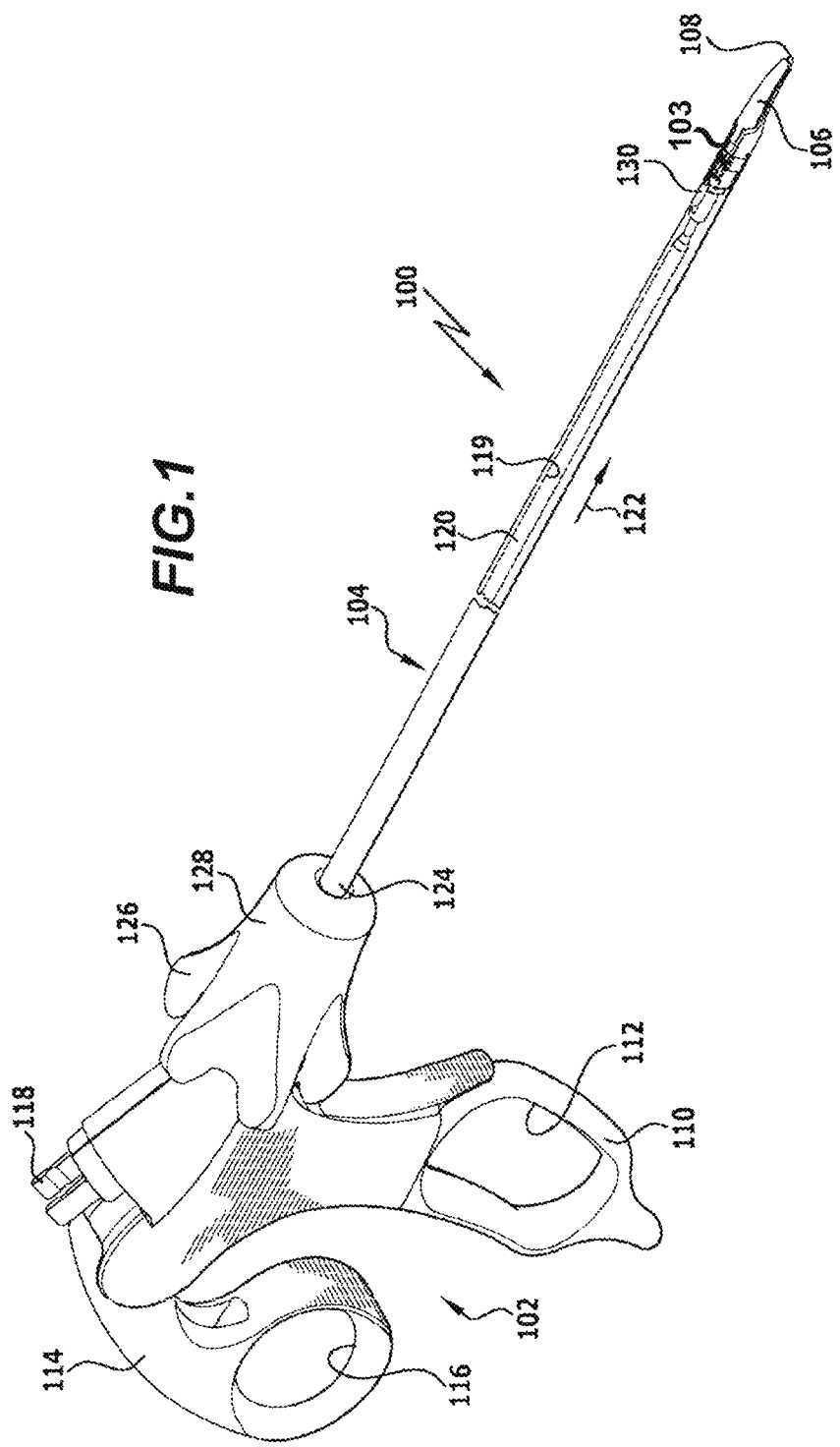
FIG. 1 shows a schematic perspective representation of a surgical instrument.

Like or functionally equivalent features are provided with like reference numerals in the individual figures.

Figure 2:
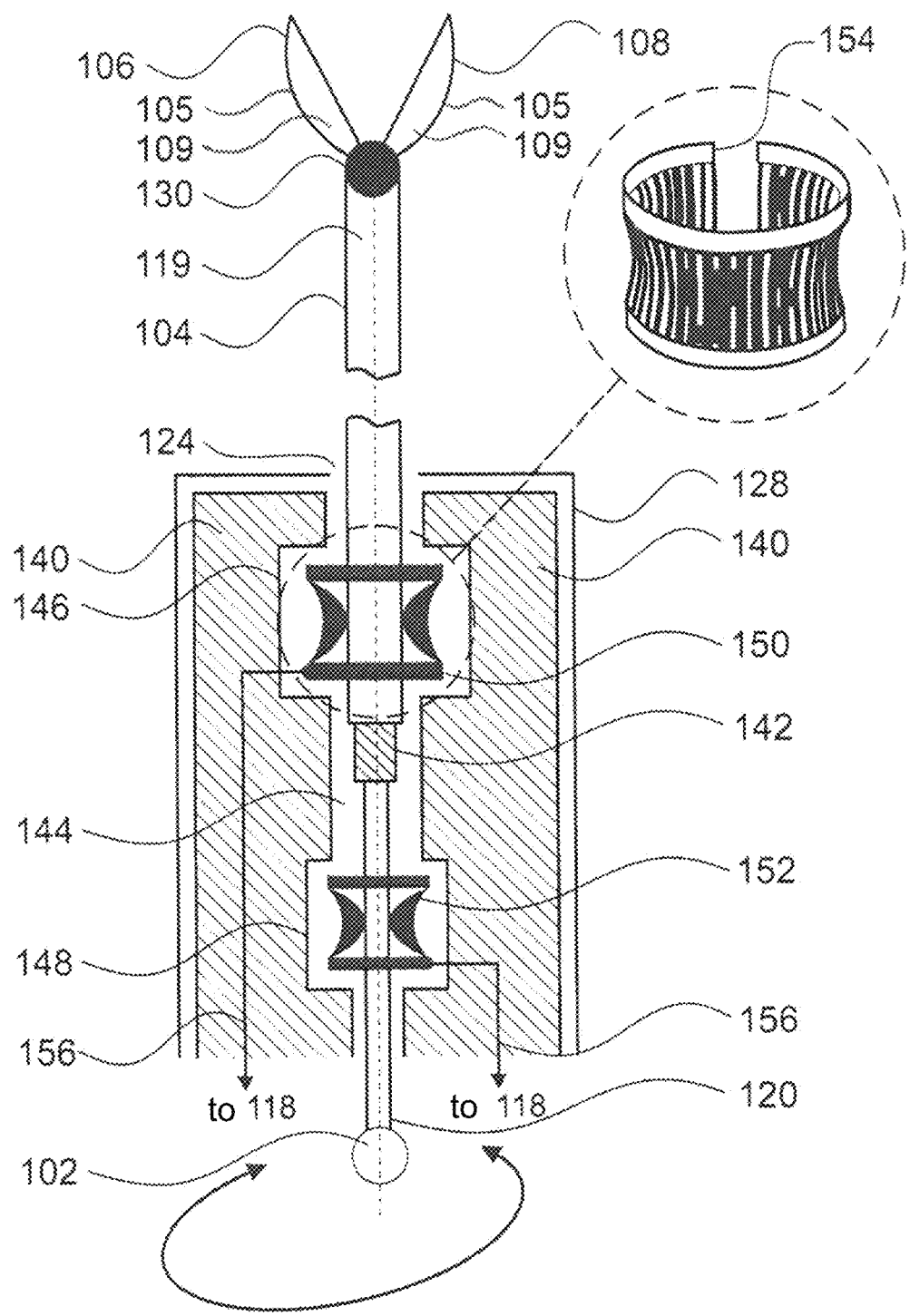
FIG. 2 shows a simplified sectional view of a first embodiment of a connection device for connecting a tubular shank section to a hand piece of the surgical instrument.
Figure 3:
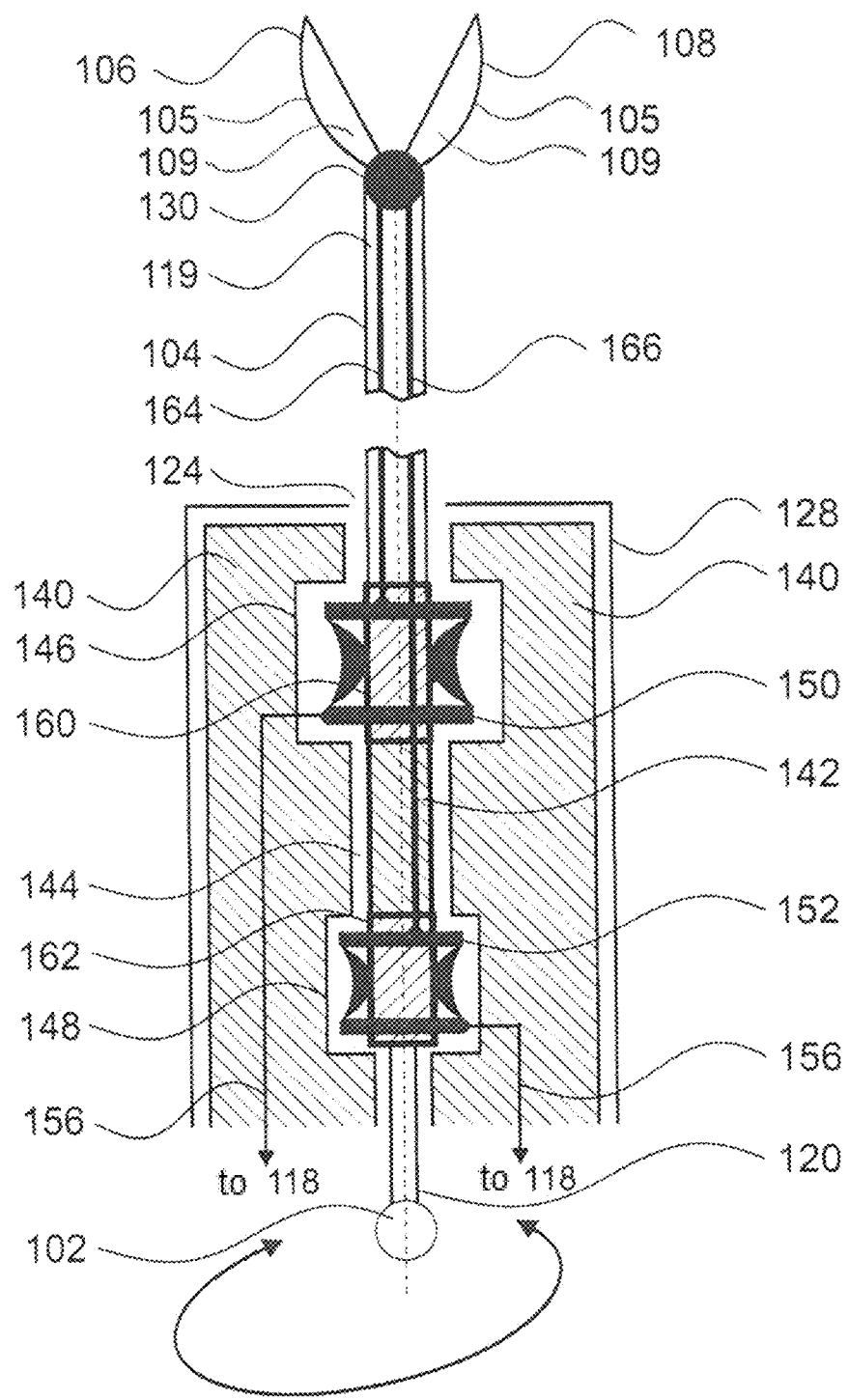
FIG. 3 shows a simplified sectional view of a second embodiment of the connection device for connecting the tubular shank section to the hand piece of the surgical instrument.

A surgical instrument 100 exemplified in FIGS. 1 to 3 comprises a hand piece/handle 102, a tool 103 having a tubular shank 104 including an internal force transmission device 120, a first branch 106 and a second branch 108.

The hand piece 102 has a fixed grip piece 110 including a finger opening 112 and a movable operating lever 114 including a finger opening 116. A surgeon, for example, may grip the handle 102 and may operate the first branch 106 and/or the second branch 108 on a tool head 105 by a movement of the movable lever 114 relative to the fixed grip piece 110 by means of the force transmission device 120.

Furthermore, the hand piece 102 comprises electric terminals 118 for contacting and/or for applying a voltage. From the terminals 118 electrical connections lead to the first branch 106 and/or the second branch 108 and supply the latter or electrodes 109 disposed thereon (not shown in detail) with current.

The tubular shank 104 is configured to be substantially rotationally symmetric about a central axis and comprises a cylindrical cavity 119. The tubular shank 104 is thus in the form of an elongate shank for minimally invasive use of the instrument.

The hand piece 102 is connected/coupled to the tubular shank 104 and a pull/push rod 120 which is guided in the cylindrical cavity 119 of the tubular shank 104 and forms the force transmission device, wherein a movement in a force transmission direction (axial direction) 122 of the pull/push rod 120 relative to the tubular shank 104 and/or a rotational movement of the pull/push rod 120 relative to the tubular shank 104 is ensured. Especially, the pull/push rod 120 may be linked to the hand piece 102 coupled in a rotationally fixed or rotational manner, and the tubular shank 104 may be supported on the hand piece 102 about an axis extending in parallel to the force transmission device 122 in a rotationally fixed or rotational manner.

For rotating the tubular shank 104 about the axis aligned in parallel to the force transmission device 122 in the example illustrated in FIG. 1 an actuating device 128 in the form of a rotary element/rotary knob 126, for example, is provided at a proximal end 124 of the tubular shank 104 facing the hand piece 102. By means of the actuating device 128 a surgeon who operates the surgical instrument 100 can rotate the tubular shank 104 especially easily about the axis (shank axis) aligned in parallel to the force transmission device 122. At a distal end 130 of the tubular shank 104 facing away from the hand piece 102 the first branch 106 and the second branch 108 are arranged to be pivoting relative to each other.

While such actuating device 128 basically may also be provided in accordance with the invention so as to be able to carry out, e.g. use-oriented, a manual rotation of the tubular shank 104 for guiding the same at the patient or for aligning and/or adjusting the same, according to the invention the actuating device 128 further includes a connection device as part of an insert system for at least temporarily receiving a tool intended for single use (single-use tool). Alternatively, also merely the connection device may be provided without the functionality of the actuating device 128 and/or of the rotary element 126, for example when the actuating functions thereof are not required or are not intended to be provided in terms of constructional design. To simplify matters, hereinafter and with respect to the aforementioned alternatives also the connection device is denoted with the reference numeral 128.

FIG. 2 illustrates a simplified sectional view of a first embodiment of the connection device 128 for connecting the tubular shank 104 to the hand piece 102 (not shown in FIG. 2 or reduced to a circular element) of the surgical instrument. In the figurative sense, furthermore in FIG. 2 the first branch 106, the second branch 108, the cylindrical cavity 119, the proximal end 124 and the distal end 130 are corresponding to the positions shown in FIG. 1.

In accordance with FIG. 2, on the inside of the connection device 128 encased in the handle, which for the rest preferably has a round or cylindrical and a rotationally symmetrical design without being restricted to a particular external shape, however, insulating elements 140 and 142 are provided which form a chuck of the handle for the tubular shank 104. The insulating element 140 preferably consists of at least one molded piece and advantageously of plural, for example two, molded pieces made from an electrically insulating material suited for use in medical engineering, for example plastic, resin, rubber or caoutchouc, or ceramic, without being restricted thereto. An insulation may also be materialized, for example, by means of an electrically insulating coating.

The insulating element 140 is adapted, as regards its size, to the internal volume of the connection device 128 and to the space required by the tubular shank 104, i.e. on the one hand it substantially fills free volume of the connection device 128 (distal section of the handle) up to the outer periphery thereof (handle housing), and moreover includes a receiving shaft 144 towards the central axis of the tubular shank 104 and, extending along the longitudinal direction thereof and circularly concentrically about the central axis of the tubular shank 104, in addition at least a first recess 146 and a second recess 148 for receiving a first contact lamella device 150 and, resp., a second contact lamella device 152. It is pointed out in this context that the insulating element 140 may also be formed integrally (in one material piece) with the handle housing.

Each of the contact lamella devices (or else clamping sleeves) 150, 152 is primarily made from a metal and is coated e.g. with nickel, silver or gold, without being restricted thereto, however, for low contact resistance and high ampacity and may be configured as an annular stamped part in leaf-spring technique or as a wicker basket structure. For the purpose of better illustration, in FIG. 2 a contact lamella device 154 of the afore-mentioned type is symbolized in detail in a circle of a broken line.

In the first embodiment of the connection device 128 the first contact lamella device 150 may be accommodated in an e.g. cage-type rigid spring cage component (not shown) which is arranged to be stationary in the first recess 146. The rigid spring cage ensures that the first contact lamella device 150 is largely free from impacting forces and in so far is unloaded in the non-equipped state of the connection device 128.

In a state of the connection device 128 equipped with the tubular shank 104, the individual contact lamellas of the first contact lamella device 150 are pressurized through the outer diameter of the tubular shank 104 radially outwardly with a pressure force which elastically forces the contact lamellas outwardly evenly spread over the periphery by the fact that the outer diameter of the tubular shank 104 is larger than the smallest inner diameter of the unloaded contact lamella device 150. In response thereto, the first contact lamella device 150 generates a holding force acting on the periphery of the tubular shank 104 (friction fit). Said holding force, i.e. a stretching effect of the contact lamella device 150 on the tubular shank 104 is designed to be sufficiently high so that the entire tubular shank 104 is axially fixed in the connection device 128 or the hand piece 102 during use of the surgical instrument, and is selected to be sufficiently low so that, after use of the surgical instrument, the tubular shank 104 can be removed or detached from the connection device 128 or the hand piece 102 again and can also rotated within the handle, where appropriate.

The tubular shank 104 may be provided, for backing the holding force and the axial fixation in the connection device 128, at its outer periphery with a groove-like formation or recess being circumferential at least in parts, alternatively annularly, in which lamellas of the first contact lamella device 150 may resiliently lock in engagement. Advantageously, an engagement which is detectable in a tactile and/or audible manner is achieved at a predetermined axial relative position so that also feedback regarding the reaching of the predetermined axial position of the tubular shank 104 in the connection device 128 can be obtained.

In the first embodiment of the connection device 128, furthermore the second contact lamella device 152 is configured as an (axially acting) sliding contact about the pull/push rod 129 and as such is arranged stationarily in the second recess 148. The second contact lamella device may equally be received in a cage-type rigid spring cage (not shown) which ensures that the second contact lamella device 152 in the non-equipped state of the connection device 128 (not tool inserted in the chuck) is largely free from impacting forces and in so far is unloaded.

In the state of the connection device 128 equipped with the tubular shank 104, the individual contact lamellas of the second contact lamella device 152 are radially pressurized through the outer diameter of the pull/push rod 120 with a pressure force which forces the contact lamellas evenly spread over the periphery radially outwardly by the fact that the outer diameter of the pull/push rod 120 is larger than the smallest inner diameter of the unloaded contact lamella device. In response thereto, the second contact lamella device 152 generates a clamping force acting on the periphery of the pull/push rod 120 (friction fit). Said clamping force, i.e. a clamping effect of the second contact lamella device 152 on the pull/push rod 120, is dimensioned to be so low that a permanent sliding contact with the pull/push rod 120 movable in the longitudinal direction and optionally rotationally is provided.

Along with the generation of the holding force by the first contact lamella device 150 and the generation of the clamping force by the second contact lamella device 152, current is supplied to the tubular shank 104 at the outer periphery thereof in the first recess 146 by the first contact lamella device 150 and current is supplied to the pull/push rod 120 at the outer periphery thereof in the second recess 148 by the second contact lamella device 152. For avoiding short-circuit, the tubular shank 104 (outer tube) and the pull/push rod 120 are radially insulated against each other by the insulating element 142. Further, for supplying current to the bipolar tubular shank instrument, each of the first contact lamella device 150 and the second contact lamella device 152 is provided with conducting connectors 156 which are guided away from the contact lamella devices 150, 152 and, extending through the insulator element 140, toward the terminals 118 at the hand piece 102.

In other words, current is supplied to the bipolar tubular shank 104 and, resp., the tool 103 in the connection device 128 and, resp., the hand piece 102 via two contact lamella devices 150, 152. A contact lamella device 152 having a lower force is located on the pull/push rod 120. The other contact lamella device 150 having a high force is located at the outer tube of the tubular shank 104. The two parts (outer tube and pull/push rod) are insulated against each other. The force of the other contact lamella device 150 is sufficiently high to axially fix the entire tubular shank 104 in the hand piece 102 during use. It is moreover sufficiently low to detach the tubular shank 104 from the hand piece 102 again. The pull/push rod 120 is supplied with current via the sliding contact of the one contact lamella device 152 and may be axially displaced at the sliding contact without the electric contact being interrupted. The tubular shank 104 can preferably be rotated within the hand piece 102.

FIG. 3 illustrates a simplified sectional view of a second embodiment of the connection device 128 for connecting the tubular shank 104 to the hand piece 102 (not shown in FIG. 3 or reduced to a circular element) of the surgical instrument. In the figurative sense, also in FIG. 3 the first branch 106, the second branch 108, the cylindrical cavity 119, the proximal end 124 and the distal end 130 correspond to the positions shown in FIG. 1.

According to FIG. 3, at the inside of the connection device 128 encased in the handle, which for the rest preferably has a round or cylindrical and rotationally symmetrical design without being limited to a particular external shape, however, insulating elements 140 and 142 are provided. The insulating element 140 preferably consists of at least one molded piece and advantageously of plural, for example two, molded pieces made from an electrically insulating material suited for use in medical engineering, for example plastic, resin, rubber or caoutchouc or a ceramic, without being limited thereto.

The insulating element 140 is adapted, as to its size, to the inner volume of the connection device 128 (corresponding to the distal portion of the handle) and to the space required by the tubular shank 104, i.e. on the one hand it substantially fills free volume of the connection device 128 up to the outer periphery thereof (handle housing) and moreover includes, towards the central axis of the tubular shank 104, a receiving shaft 144 and, extending along the longitudinal direction thereof and circularly concentric about the central axis of the tubular shank 104, in addition at least a first recess 146 and a second recess 148 for receiving each of a first contact lamella device 150 and a second contact lamella device 152. In this case, too, the connection device 128 may be formed in one (material) piece with the handle.

The first and second contact lamella devices 150, 152 are primarily made from a metal and are coated e.g. with nickel, silver or gold without being limited thereto, however, for low contact resistance and high ampacity and may be configured, for example, as an annular stamped part in leaf-spring technique or as a wicker basket. The contact lamella device 154 of the a.m. type shown in FIG. 2 for the purpose of better illustration is omitted in FIG. 3, although the same basic structure may be used in FIG. 3.

In the second embodiment of the connection device 128, the first contact lamella device 150 is received in an e.g. cage-type rigid spring cage component (not shown) which is arranged stationarily in the first recess 146, and the second contact lamella device 152 is received in an e.g. equally cage-type rigid spring cage component (not shown) which is stationarily arranged in the second recess 148. The rigid spring cages ensure that the first and second contact lamella devices 150, 152 in the non-equipped state of the connection device 128 are largely free from impacting forces and in so far are unloaded.

Further, in the second embodiment at the outer periphery of the tubular shank 104 (but not at the force transmission device supported therein) a first contact bushing device 160 and a second contact bushing device 162 are arranged to be axially corresponding to each of the recesses 146, 148, i.e. at a first axial position of the first contact lamella device 150 and at a second axial position of the second contact lamella device 152, and being electrically insulated against the tubular shank 104 by the insulating element 142. In a state of the connection device 128 equipped with the tubular shank 104, the individual contact lamellas of the first and second contact lamella devices 150, 152 are pressurized through the outer diameter of the contact bushing devices 160, 162 with a radial pressure force which forces the contact lamellas evenly spread over the periphery outwardly by the fact that the outer diameter of the contact bushing devices 160, 162 is larger than the smallest inner diameter of the unloaded contact lamella device. In response thereto, the first and second contact lamella devices 150, 152 generate a holding force acting on the periphery of the contact bushing devices 160, 162. Said holding force, i.e. a clamping effect of the contact lamella devices 150, 152 on the contact bushing devices 160, 162 and thus also on the tubular shank 104, is designed to be sufficiently high so that during use of the surgical instrument the entire tubular shank 104 is axially fixed in the connection device 128 and, resp., in the hand piece 102, and is selected to be sufficiently low so that after use of the surgical instrument the tubular shank 104 can be removed or detached from the connection device 128 and, resp., from the hand piece 102 and is optionally rotatable.

The tubular shank 104 or the contact bushing devices 160, 162 may be provided, for backing the holding force and the axial fixation in the connection device 128, at the respective outer periphery with a groove-type formation being circumferential at least in parts, alternatively annularly, in which lamellas of the first and/or the second contact lamella device 150, 152 can resiliently lock. Advantageously, in this way engagement which is detectable in a tactile and/or audible manner at a predetermined position is achieved so that also a feedback regarding the reaching of a predetermined position of the tubular shank 104 in the connection device 128 can be obtained.

In the second embodiment of the connection device 128, in contrast to the first embodiment, both spring cages or contact lamella devices 150, 152 are provided for generating a holding force so that both spring cages or contact lamella devices 150, 152 jointly fix the tool 103 axially in the hand piece 102 and no sliding contact (during interaction with the force transmission device) without any contribution to the total holding force is required.

Along with the generation of the axial holding force by the first contact lamella device 150 and the generation of the axial holding force by the second contact lamella device 152, the first contact lamella device 150 supplies current to the first branch 106 via the first contact bushing device or (sleeve-type) bushing 160 arranged on the periphery of the tubular shank 104 and insulated against the tubular shank 104 which is connected, for carrying current by means of a first conductor connection 164, for example a strand inside the tubular shank coated in an insulating manner, to the first branch 106, and the second contact lamella device 152 supplies current to the second branch 108 via the second contact bushing device or (sleeve-type) bushing 162 equally arranged on the periphery of the tubular shank 104 and insulated against the tubular shank 104 which is connected, for carrying current by means of a second conductor connection 166, for example a strand inside the tubular shank coated in an insulating manner, to the second branch 108.

That is to say, for avoiding short-circuit the tubular shank 104 (external tube) and the first and second contact bushing devices or bushings 160, 162 are insulated against each other, e.g. by the insulating element 142 which in this case extends at least from the distal end of the first contact bushing device 160 to the proximal end of the second contact bushing device 162 beneath the latter on the outer periphery of the tubular shank 104. For supplying the bipolar tubular shank instrument with current moreover each of the first contact lamella device 150 and the second contact lamella device 152 is provided with conductive connections 156 which are guided away from the contact lamella devices 150, 152 and, extending through the insulator element 140, to the terminals 118 at the hand piece 102.

In other words, current is supplied to the bipolar tubular shank instrument in the connection device 128 and, resp., the hand piece 102 via the two contact lamella devices 150, 152, two bushings 160, 162 and two conductors 164, 166 connected to the two bushings 160, 162 and leading, starting from the two bushings 160, 162, through the tubular shank 104 to each of the first and second branches 106, 108 so that it is not the pull/push rod 120 and the external tube but the strands connected to the bushings in the external tube which conduct the current, wherein both spring cages jointly fix the tool axially in the connection device 128 and, resp., in the hand piece 102. In this case, a sliding contact which might be susceptible to dirt and wear, and thus susceptible to interference, at the pull/push rod 120 is not required. The force of the two contact lamella devices 150, 152 is sufficiently high for the total tubular shank 104 to be axially fixed in the hand piece 102 during use. It is moreover sufficiently low for the tubular shank 104 to be detached from the hand piece 102 again. The tubular shank 104 can be rotated within the hand piece 102.

Preferably, two identical spring cages and/or contact lamella devices 150, 152 are used, with the holding force being divided approximately in half. It is alternatively possible, however, to arrange different spring cages or contact lamella devices 150, 152 with the holding force then being differently divided, so as to be able to correspond to constructional peculiarities and/or size ratios on the connection device 128 and/or on the hand piece 102, for example.

Hence, in the foregoing an insert system in the form of a connection device 128 or a coupling device on a hand piece 102 of a bipolar surgical instrument for connecting and disconnecting a tubular shank 104 supplied with current and provided for single-use and the reusable hand piece 102 by means of contact lamellas has been described. The connection enables a rotational movement, the supply of current to the tool via a fixed contact and a sliding contact, alternatively without any sliding contact via two fixed contacts, as well as the axial fixation of the tubular shank 104 within the hand piece 102 against inadvertent falling-out.

It is understood that in the afore-described embodiment of a bipolar surgical instrument further insulation points for electrical insulation of current-carrying or potential-carrying parts or sections may be provided at appropriate positions. It is further understood that merely an exemplary nature is attributed to the described embodiments and, in this respect, modifications may easily result for those skilled in the art without the scope of protection defined by the attached claims being left. Such modifications may relate especially to the type and the functioning of the first and second branches 106, 108 and/or the physical configuration of the connection device 128 and/or the hand piece 102. Equally, components such as spring cages, contact lamella (devices), bushings, tubular shank, pull/push rod, insulation and the like are not subjected to any particular limitations as regards material and shaping as long as the effect and the functionality according to the invention are provided and achieved by said components.

The invention claimed is:

1. A handle for a bipolar surgical instrument, the handle comprising a current application device for applying electric current to a tool by a power switch arranged on the handle, the handle further comprising a chuck, the tool being mechanically insertable into and detachable from the chuck at a tubular shank thereof and can be electrically coupled in and out at the current application device, the chuck including two receiving/bearing elements which are axially spaced in an inserting direction of the tubular shank, are radially elastically yielding, and are electrically insulated against each other for radially and/or axially guiding and/or securing the tubular shank, the two receiving/bearing elements electrically connected to the current application device to transmit electric current to the tool, wherein at least one of the two receiving/bearing elements includes a radially inwardly directed projection or a radially inwardly directed bulge, wherein the radially inwardly directed projection or the radially inwardly directed bulge is adapted to get into locking engagement with a radial notch/undercut for axially securing the tubular shank in the chuck of the handle, and wherein the chuck defines an inner wall facing the tool and recesses in the inner wall for receiving the two receiving/bearing elements inside the inner wall.

2. The handle according to claim 1, wherein each of the two receiving/bearing elements forms a radially elastically extendable shank boot in a form of a slip ring, a ball bearing having radially elastically movable balls, or a spring/lamella cage.

3. The handle according to claim 1, wherein the two receiving/bearing elements are adapted to exert differently high radial forces on the tool.

4. The handle according to claim 1, wherein each of the two receiving/bearing elements is configured to exert a clamping force on the tubular shank to create a friction fit.

5. The handle according to claim 1, wherein the two receiving/bearing elements comprise a first receiving/bearing element configured to exert a first radial force on the tubular shank and a second receiving/bearing element configured to exert a second radial force on the tubular shank less than the first radial force.

6. An electro-surgical instrument of a bipolar design, the electro-surgical instrument comprising:

a handle comprising a current application device for applying electric current to a tool by a power switch arranged on the handle, the handle further comprising a chuck, the tool being mechanically insertable into and detachable from the chuck at a tubular shank thereof and can be electrically coupled in and out at the current application device, the chuck including two receiving/bearing elements which are axially spaced in an inserting direction of the tubular shank, are radially elastically yielding, and are electrically insulated against each other for radially and/or axially guiding and/or securing the tubular shank, the two receiving/bearing elements electrically connected to the current application device to transmit electric current to the tool; and the tool adapted to be inserted in the handle, the tool comprising a tool head studded with or including electrodes at a distal end of the tubular shank, a proximal end of the tubular shank being insertable into the chuck of the handle, wherein the tubular shank includes two shank sections which are axially spaced and electrically insulated against each other and which are adapted to get into mechanical guiding and/or securing engagement and simultaneously into electrical contact with the two receiving/bearing elements in the chuck of the handle to connect the electrodes at the tool head to the current application device, wherein at least one of the two receiving/bearing elements includes a radially inwardly directed projection or a radially inwardly directed bulge, wherein the radially inwardly directed projection or the radially inwardly directed bulge is adapted to get into locking engagement with a radial notch/undercut for axially securing the tubular shank in the chuck of the handle, and wherein the chuck defines an inner wall facing the tool and recesses in the inner wall for receiving the two receiving/bearing elements inside the inner wall.

7. The electro-surgical instrument according to claim 6, wherein the handle is designed as a reusable article and the tool is designed as a single-use article.

8. The electro-surgical instrument according to claim 6, wherein the two receiving/bearing elements acting on an outer shank element of the tubular shank are in a form of a quasi fixed contact and the two receiving/bearing elements acting on an inner shaft element are in the form of an at least axially acting sliding contact.

9. A handle for a bipolar surgical instrument, the handle comprising a current application device for applying electric current to a tool by a power switch arranged on the handle, the handle further comprising a chuck that defines a receiving shaft with an inner wall, the tool being mechanically insertable into the receiving shaft and detachable from the chuck at a tubular shank thereof, the chuck including two receiving/bearing elements that are axially spaced in an inserting direction of the tubular shank and are electrically insulated from each other for radially and/or axially guiding and/or securing the tubular shank, the two receiving/bearing elements being electrically connected to the current application device to transmit electric current to the tool, at least one of the two receiving/bearing elements having a radially inwardly directed portion and being located in a recessed section of the receiving shaft that forms a space between the radially inwardly directed portion and the inner wall, the radially inwardly directed portion having an inner diameter configured to elastically expand radially outwardly relative to the inner wall and into the space when the tubular shank is inserted through the at least one of the two receiving/bearing elements, the radially inwardly directed portion configured to generate a radial clamping force on the tubular shank when the tubular shank is inserted through the at least one of the two receiving/bearing elements.

10. The handle according to claim 9, wherein the receiving shaft defines a first radial width and the recessed section defines a second radial width that is larger than the first radial width.

\* \* \* \* \*